(12) United States Patent
Prager et al.

(10) Patent No.: US 7,247,157 B2
(45) Date of Patent: Jul. 24, 2007

(54) IMPLANT FOR OSTEOSYNTHESIS

(75) Inventors: Ronald Prager, Bovenau (DE); Nils Zander, Eckernförde (DE)

(73) Assignee: Stryker Trauma GmbH (DE)

( * ) Notice: Subject to any disclaimer, the term of this patent is extended or adjusted under 35 U.S.C. 154(b) by 429 days.

(21) Appl. No.: 10/755,815

(22) Filed: Jan. 12, 2004

(65) Prior Publication Data

US 2004/0158252 A1    Aug. 12, 2004

(30) Foreign Application Priority Data

Jan. 23, 2003   (DE) ................. 203 00 987 U

(51) Int. Cl.
*A61B 17/58*    (2006.01)
(52) U.S. Cl. ....................................... 606/64
(58) Field of Classification Search .......... 606/60, 606/62, 63, 64, 65, 66, 67, 68, 61
See application file for complete search history.

(56) References Cited

U.S. PATENT DOCUMENTS

| | | | |
|---|---|---|---|
| 2,376,089 A * | 5/1945 | Savageau ............ 411/81 |
| 5,112,333 A | 5/1992 | Fixel | |
| 5,472,444 A | 12/1995 | Huebner et al. | |
| 5,484,438 A | 1/1996 | Pennig et al. | |
| 5,520,688 A * | 5/1996 | Lin ............... 606/61 |
| 5,709,686 A * | 1/1998 | Talos et al. ............ 606/69 |
| 5,776,194 A | 7/1998 | Mikol et al. | |
| 5,876,402 A | 3/1999 | Errico et al. | |
| 5,879,389 A | 3/1999 | Koshino | |
| 5,931,838 A * | 8/1999 | Vito ............... 606/61 |
| 5,954,722 A * | 9/1999 | Bono ............. 606/61 |
| 6,004,323 A | 12/1999 | Park et al. | |
| 6,261,291 B1 | 7/2001 | Talaber et al. | |
| 6,454,770 B1 * | 9/2002 | Klaue ............. 606/69 |
| 6,602,255 B1 | 8/2003 | Campbell et al. | |
| 6,702,816 B2 | 3/2004 | Bühler | |
| 2004/0087951 A1* | 5/2004 | Khalili ............ 606/69 |

* cited by examiner

*Primary Examiner*—Edjardo C. Robert
*Assistant Examiner*—Nicholas Woodall
(74) *Attorney, Agent, or Firm*—Lerner, DAvid, Littenberg, Krumholz & Mentlik, LLP

(57) ABSTRACT

An implant for osteosynthesis, for example a bone nail, has an implant body which has at least one bore with a threaded portion and a bone screw which engages the thread when it is threaded into a bone for the fixation of the implant body. The threaded bore has an annular groove the diameter of which is larger than the thread outer diameter, and which receives a ring of a deformable material with an inner diameter which is smaller than the outer diameter of the thread of the bone screw so that the ring extends partially into the bore.

29 Claims, 2 Drawing Sheets

IMPLANT FOR OSTEOSYNTHESIS

BACKGROUND OF THE INVENTION

It is generally known to fix plates to bone by means of bone screws for the repair of bone fractures. Further, it is well known to configure bone screws for use with so-called interlocking nails for the care of fractures of tubular bones. Interlocking nails have cross-bores for the reception of bone screws or interlocking screws at both the distal and proximal nail ends. It is known to provide the bores with a thread for the reception of a bone screw. In most cases, the thread is a so-called cortical thread, i.e. a thread corresponding to the thread of the bone screw. This thread has the advantage that it impedes the postoperative migration of the bone screws.

It is known to configure nails for the repair of humeral fractures as interlocking nails and to provide several cross-bores in the proximal portion of the interlocking nail which are offset from each other in the circumferential direction and extend obliquely to the axis of the nail, if required. A nail having oblique cross-bores is shown in U.S. Pat. No. 5,472,444. The emigration of interlocking screws is critical and, thus, is a particular problem in a humeral fracture.

SUMMARY OF THE INVENTION

It is one object of the invention to provide an implant for osteosynthesis that efficiently prevents the postoperative migration of bone screws.

In the inventive implant, the threaded bore has an annular groove the diameter of which is larger than the thread outer diameter, and which receives a ring of a deformable material with an inner diameter which is smaller than the outer diameter of the thread of the bone screw. Thus, the ring has a portion which extends into the threaded bore.

According to the invention, the ring is preferably made of a plastic material, e.g. polyethylene. After insertion into the annular groove the ring blocks some portion of the thread cross-section and, while the bone screw is turned in, the ring is deformed so as to produce a frictional engagement between the bone screw, the ring and the annular groove, that prevents the bone screw from turning out by itself.

Moreover, the ring centers the bone screw in the threaded bore so that an increased angular stability of the bone screw is achieved in the implant as compared to that of the non-secured design.

The bores in the implant usually have an inlet end and an outlet end. According to an aspect of the invention, the annular groove is disposed adjacent to the outlet end. According to another aspect of the invention, the bore portion between the outlet end and annular groove preferably is non-threaded. According to an aspect of the invention, the bore portion adjacent to the inlet end is also non-threaded. The arrangement of the ring at the outlet side of the through bore ensures that the screw is already in a threaded engagement when it strikes the ring. Here, the mostly conical tip of the bone screw urges the ring into the groove before the ring of the bone screw undergoes deformation. This ensures that the interlocking screw does not force the ring out of the bore.

According to another aspect of the invention, the annular groove is rectangular in cross-section with the ring exhibiting a complementary cross-section. However, it is preferred that the width of the ring be somewhat smaller than the width of the annular groove. This allows easier insertion of the ring into the annular groove. Also, this creates a clearance for an axial deformation of the ring.

According to another aspect of the invention, the ring is split and the ends of the ring are at a distance from each other when the ring is in a relaxed state. During its insertion, the ring may be slightly contracted radially to enable it to be inserted into the annular groove without a problem. Preferably, the two inside edges of the ring are chamfered to prevent the ring from being forced out of the groove. Basically, it would be sufficient to chamfer the edge facing the inlet end, but since it is desired that the orientation in which the ring is inserted into the groove does not matter it is preferred to form both inner edges with a chamfer.

The outer diameter of the ring, when in a relaxed state, is slightly larger than the diameter of the annular groove. This causes the ring to be retained by itself in the groove, i.e. also during transport and while the implant is handled before the bone screw is turned in.

The invention is applicable to any implants that are inserted in combination with bone screws. The invention is specifically preferred for use with an intramedullary implant, e.g. a bone nail, preferably an interlocking nail. It is particularly preferred to apply it to a humeral nail, the proximal end of which has three or more cross-bores the axes of which are offset from each other in a circumferential direction.

BRIEF DESCRIPTION OF THE DRAWINGS

The invention will be described in more detail below with reference to an embodiment shown in the drawings.

DETAILED DESCRIPTION

Figure 1:
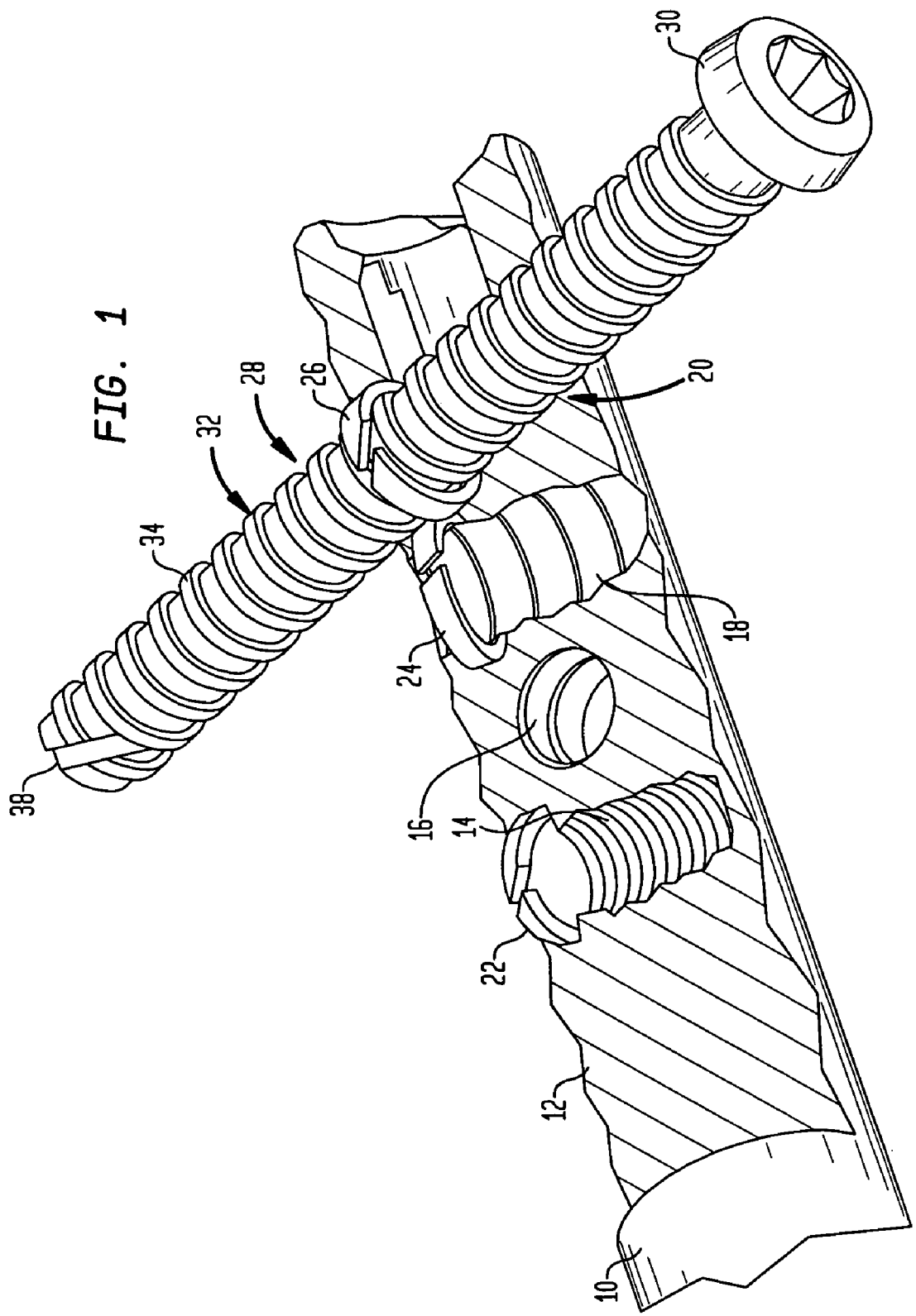
FIG. 1 shows a cross-section of the proximal end of the humeral nail with securing rings according to the invention in a perspective view.

Referring to FIG. 1 there is shown a humeral nail 10 having four offset cross-bores and having a longitudinally sectioned proximal portion 12. As can be seen, the preferred proximal portion 12 is provided with four cross-bores 14, 16, 18 and 20 which, in the preferred embodiment are offset from each other in the axial and circumferential directions and are at an angle from the longitudinal axis 21 of nail 10. In the preferred embodiment, bores 14, 16, 18 and 20 are configured as threaded bores. FIG. 1 further shows that bores 14, 18 and 20 receive a securing ring 22, 24 and 26, respectively. If desired, bore 16 can also include a securing ring. These rings serve for securing an interlocking screw 28 which has a head 30 and a shank 32 with thread 34. In the preferred embodiment thread 34 is a cortical thread which is useful in ensuring a fixed seating in the bone without unnecessarily imposing a stress on the bone. The preferred thread 34 is a flat thread which threadably engages the thread in the threaded bores 14, 16, 18 and 20.

Figure 2:
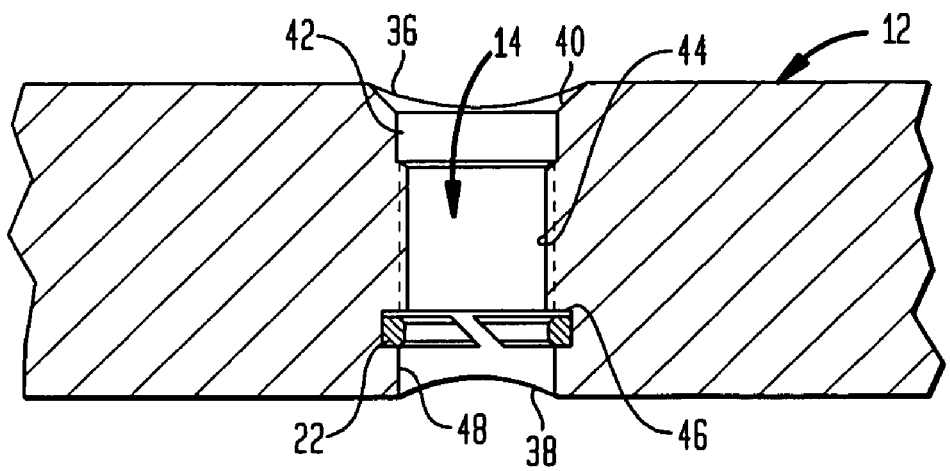
FIG. 2 shows a longitudinal section through a humeral nail with a threaded bore, a groove and a securing ring according to the invention.

FIG. 2 illustrates a single threaded bore, e.g. the threaded bore 14. This bore is typical of the other threaded bores of the preferred embodiment. Bore 14 has an inlet end 36 and an outlet end 39. Therefore, during use conical tip 38 of interlocking screw 28 shown in FIG. 1 is introduced into the inlet end 36 which has an inlet conical taper or countersink 40 as can be seen at end 36. In the preferred embodiment, countersink 40 is joined by a non-threaded bore portion 42. This is followed by threaded portion 44. Portion 44 has at its end formed therein an annular groove 46 of a rectangular cross-section in which securing ring 22 is received. Again, in the preferred embodiment, non-threaded portion 48 is located towards outlet end 39. As can be seen the width of ring 22 is somewhat smaller than the width of annular groove 46.

Figure 3:
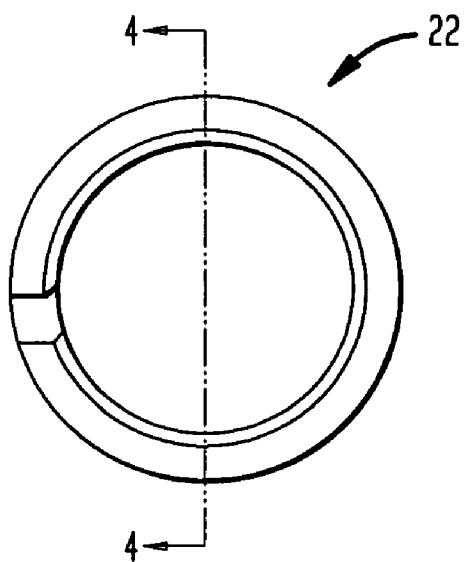
FIG. 3 shows the front view of a securing ring of FIG. 1 or 2.
Figure 4:
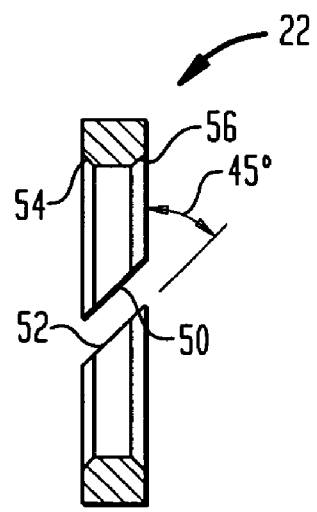
FIG. 4 shows a section through the ring of FIG. 3 along the line 4-4.

Preferred ring 22 is illustrated in somewhat more detail in FIGS. 3 and 4. As can be seen in the preferred embodiment, ring 22 is split and ends 50, 52 are provided with a slope at an angle of 45° are spaced a certain distance from each other. The inside edges of ring 22 are provided with chamfer 54 and 56, respectively. The outer diameter of ring 22, when in a relaxed state, is slightly larger than the diameter of annular groove 46. In the preferred embodiment, the inner diameter of the ring is smaller than the outer or major diameter of threaded portion 34, but is larger than the inner or minor diameter of threaded portion 34 of screw 28.

While being inserted, ring 22 is somewhat compressed circumferentially so that it can be readily introduced into annular groove 46. After insertion into groove 46, ring 22 will relax and expand to a small extent after insertion, but not up to its fully expanded diameter in the relaxed state. This results in the ring being retained in the annular groove 46 to a fairly reliable degree.

When an interlocking screw 28 is introduced into bore 14 from inlet end 36, threads 44 and 34 engage each other before thread 34 interacts with securing ring 22. Conical tip 38 of interlocking screw 28 initially urges securing ring 22 radially outwardly before thread 34 interacts with securing ring 22 so that forcing ring 22 out of the bore is avoided. The ring, which is made of an elastic plastic material, is deformed accordingly and frictional engagement is produced between thread 34 and ring 22 and between ring 22 and annular groove 46, the result obtained being that screw 28 is efficiently secured in bore 34.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant for osteosynthesis, comprising a bone nail having a body which has at least one bore with a threaded portion and a bone screw which engages the threaded portion when it is threaded into a bone for the fixation of the implant body, wherein the bore has an annular groove the diameter of which is larger than an outer diameter of the thread and a ring of a deformable material for insertion into the groove, the ring having an inner diameter which is smaller than the outer diameter of the thread of the bone screw, wherein the bore has a screw inlet end and a screw outlet end and the annular groove is disposed adjacent to the outlet end, wherein a bore portion between the annular groove and the outlet end is non-threaded.

2. The implant as set forth in claim 1 further including a non-threaded bore portion adjacent to the inlet end.

3. The implant as set forth in claim 2 wherein the non-threaded portions are of a diameter which is slightly larger than the outer diameter of the bore thread.

4. The implant as set forth in claim 1 wherein the annular groove is rectangular in cross-section.

5. The implant as set forth in claim 1 wherein the ring is formed from a resiliently yielding plastic.

6. The implant as set forth in claim 1 wherein the ring is split and ends of the split ring are spaced from each other when it is in a relaxed state.

7. The implant as set forth in claim 6 wherein the ends of the ring are at an oblique angle and have the same angle of inclination.

8. The implant as set forth in claim 1 wherein a ring inner diameter has edges which have a chamfer.

9. The implant as set forth in claim 1 wherein the ring has a width which is slightly smaller than a width of the annular groove.

10. The implant as set forth in claim 9 wherein an outer diameter of the ring, when in a relaxed state, is slightly larger than a maximum diameter of the annular groove.

11. The implant as set forth in claim 1 wherein the bone nail is an interlocking nail.

12. The implant as set forth in claim 1 wherein the nail is a humeral nail, a proximal end of which has a plurality of cross-bores, the cross-bores each extending along an axis which are offset from each other in a circumferential direction.

13. A bone fracture fixation device comprising:
a bone nail having a body extending along a longitudinal axis and having at least one bore extending in a direction transverse to said axis, said bore having an inner surface with an annular groove formed therearound, said groove having one side open to said bore; and
a plastic ring mounted in said groove having an inner portion extending from said one side of said groove into said bore; and
a bone screw having a threaded outer diameter engageable with the inner portion of said ring upon insertion into said bore, wherein the ring is split and ends of the split ring are spaced from each other when it is in a relaxed state, wherein the ends of the ring are at an oblique angle and have the same angle of inclination.

14. The fracture fixation device as set forth in claim 13 wherein said bore is threaded.

15. The fracture fixation device as set forth in claim 14 wherein the annular groove is rectangular in cross-section and extends perpendicular to a central axis of said bore.

16. The fracture fixation device as set forth in claim 13 wherein the inner portion of said ring has edges which have a chamfer.

17. The fracture fixation device as set forth in claim 13 wherein an outer diameter of the ring, when in a relaxed state, is slightly larger than a maximum diameter of the annular groove.

18. A bone fracture fixation device comprising:
a bone nail having a body extending along a longitudinal axis and having a plurality of bores extending in a direction transverse to the longitudinal axis, the bores each extending along an axis which are offset from each other in a circumferential direction about the longitudinal axis, the bore having an inner surface with an annular groove formed therearound, the groove having one side open to the bore;
a plastic ring mounted in the groove having an inner portion extending from the said one side of the groove into the bore; and
a bone screw having a threaded outer diameter engageable with the inner portion of the ring upon insertion into the bores.

19. The bone fracture fixation device as set forth in claim 18 wherein the bone nail is a humeral nail.

20. An implant for osteosynthesis, comprising an implant body which has at least one bore with a threaded portion and a bone screw which engages the threaded portion when it is threaded into a bone for the fixation of the implant body, wherein the bore has an annular groove the diameter of which is larger than an outer diameter of the thread and a ring of a deformable material for insertion into the groove having an inner diameter which is smaller than the outer diameter of the thread of the bone screw, wherein the bore has a screw inlet end and a screw outlet end and the annular groove is disposed adjacent to the outlet end, wherein a bore portion between the annular groove and the outlet end is non-threaded and further including a non-threaded bore portion adjacent to the inlet end.

21. The implant as set forth in claim 20 wherein the non-threaded portions are of a diameter which is slightly larger than the outer diameter of the bore thread.

22. The implant as set forth in claim 20 wherein the implant is a bone nail.

23. An implant for osteosynthesis, comprising a bone nail having a body which has at least one bore with a threaded portion and a bone screw which engages the threaded portion when it is threaded into a bone for the fixation of the implant body, wherein the bore has an annular groove the diameter of which is larger than an outer diameter of the thread and a ring of a deformable material for insertion into the groove, the ring having an inner diameter which is smaller than the outer diameter of the thread of the bone screw, wherein the ring is split and ends of the split ring are spaced from each other when it is in a relaxed state, wherein the ends of the ring are at an oblique angle and have the same angle of inclination.

24. An implant for osteosynthesis, comprising a bone nail having a body which has at least one bore with a threaded portion and a bone screw which engages the threaded portion when it is threaded into a bone for the fixation of the implant body, wherein the bore has an annular groove the diameter of which is larger than an outer diameter of the thread and a ring of a deformable material for insertion into the groove, the ring having an inner diameter which is smaller than the outer diameter of the thread of the bone screw, wherein a ring inner diameter has edges which have a chamfer.

25. An implant for osteosynthesis, comprising a bone nail having a body which has at least one bore with a threaded portion and a bone screw which engages the threaded portion when it is threaded into a bone for the fixation of the implant body, wherein the bore has an annular groove the diameter of which is larger than an outer diameter of the thread and a ring of a deformable material for insertion into the groove, the ring having an inner diameter which is smaller than the outer diameter of the thread of the bone screw, wherein the ring has a width which is slightly smaller than a width of the annual groove, wherein an outer diameter of the ring, when in a relaxed state, is slightly larger than a maximum diameter of the annular groove.

26. An implant for osteosynthesis, comprising a bone nail having a body which has at least one bore with a threaded portion and a bone screw which engages the threaded portion when it is threaded into a bone for the fixation of the implant body, wherein the bore has an annular groove the diameter of which is larger than an outer diameter of the thread and a ring of a deformable material for insertion into the groove, the ring having an inner diameter which is smaller than the outer diameter of the thread of the bone screw, wherein the bone nail is an interlocking nail.

27. An implant for osteosynthesis, comprising a bone nail having a body which has at least one bore with a threaded portion and a bone screw which engages the threaded portion when it is threaded into a bone for the fixation of the implant body, wherein the bore has an annular groove the diameter of which is larger than an outer diameter of the thread and a ring of a deformable material for insertion into the groove, the ring having an inner diameter which is smaller than the outer diameter of the thread of the bone screw, wherein the nail is a humeral nail, a proximal end of which has a plurality of cross-bores, the cross-bores each extending along an axis which are offset from each other in a circumferential direction.

28. A bone fracture fixation device comprising:
 a bone nail having a body extending along a longitudinal axis and having at least one bore extending in a direction transverse to said axis, said bore having an inner surface with an annular groove formed therearound, said groove having one side open to said bore; and
 a plastic ring mounted in said groove having an inner portion extending from said one side of said groove into said bore; and
 a bone screw having a threaded outer diameter engageable with the inner portion of said ring upon insertion into said bore, wherein an outer diameter of the ring, when in a relaxed state, is slightly larger than a maximum diameter of the annular groove.

29. An implant for osteosynthesis, comprising an implant body which has at least one bore with a threaded portion and a bone screw which engages the threaded portion when it is threaded into a bone for the fixation of the implant body, wherein the bore has an annular groove the diameter of which is smaller than an outer diameter of the thread and a ring of a deformable material for insertion into the groove having an inner diameter which is larger than the outer diameter of the thread of the bone screw, wherein the bore has a screw inlet end and a screw outlet end and the annular groove is disposed adjacent to the outlet end, wherein a bore portion between the annular groove and the outlet end is non-threaded, wherein the implant is a bone nail.

* * * * *